United States Patent [19]

Kolhouse et al.

[11] Patent Number: 5,506,147

[45] Date of Patent: Apr. 9, 1996

[54] NON-INVASIVE EVALUATION OF MALDIGESTION AND MALABORPTION

[76] Inventors: J. Fred Kolhouse, 480 S. York St., Denver, Colo. 80209; John C. Deutsch, 2508 E. 11th Ave., #504, Denver, Colo. 80206; Vincent Guay, 2281 Clifton Avenue, Montreal, Quebec, Canada, H4A 2N5; James P. Ounsworth, Apt. #3, 18054 Pierrefonds Blvd., Pierrefonds, Quebec, Canada, H9K 1K3

[21] Appl. No.: 345,534

[22] Filed: Nov. 28, 1994

Related U.S. Application Data

[63] Continuation of Ser. No. 53,545, Apr. 15, 1993, abandoned.

[51] Int. Cl.$^6$ .................................................. G01N 33/483
[52] U.S. Cl. ........................... 436/86; 436/56; 436/63; 436/161; 436/173
[58] Field of Search ................................. 436/56, 63, 86, 436/89, 90, 161, 173, 811, 815; 435/4; 424/2, 9

[56] References Cited

U.S. PATENT DOCUMENTS

| | | | |
|---|---|---|---|
| 3,745,212 | 7/1973 | Benneville et al. | 424/9 |
| 3,806,592 | 4/1974 | Imondi | 424/7.1 |
| 3,893,992 | 7/1975 | De Benneville | 530/323 |
| 4,202,876 | 5/1980 | Monks et al. | 424/1.1 |
| 4,203,967 | 5/1980 | Gallo-Torres | 424/9 |
| 4,276,049 | 6/1981 | Gillessen et al. | 436/111 |
| 4,279,886 | 7/1981 | Allen | 424/1.1 |
| 4,676,974 | 6/1987 | Hofmann et al. | 424/9 |
| 4,684,805 | 8/1987 | Shu-Ti Lee et al. | 250/343 |
| 5,179,027 | 1/1993 | Fisher | 436/56 |
| 5,212,096 | 5/1993 | Kolhouse et al. | 436/93 |

OTHER PUBLICATIONS

Libeer et al. Clinica Chimica Acta, vol. 115, pp. 119–123, 1981.
Pemberton et al. Clinica Chimica Acta, vol. 199, pp. 253–262, 1991.
Sherding et al. American Journal of Veterinary Research, vol. 43, No. 12, pp. 2272–2273, Dec. 1982.
Chymex package insert, Adria Laboratories, 1988.
DiMagno, E. P. (1982) Gastorenterol. 83:143–146.
Lang, C. et al. (1981) Br. J. Surg. 68:771–775.
Mitchell, C. J. et al. (1979) Scand. J. Gastroenterol. 14:737–741.
Weizman, Z. et al. (1985) Gastroenterol. 89:596–604.
Hubbard, V. S. et al. (1984) Dig. Dis. Sci. 29:881–889.
Sacher, M. et al. (1978) Arch. Dis. Childhood 53:639–641.
Hawkins, E. C. et al. (1986) Am. J. Vet. 47:567–569.
Nousia-Arvanitakis, S. et al. (1978) J. Pediatrics 92:734–737.
Gharbo, S. A. et al. (1985) Anal. Biochem. 148:228–232.
Laufer, D. et al. (1991) Gastroenterol. 101:207–213.
Koren, G. et al. (1985) Dig. Dis. Sci. 30:928–932.
Lankisch, P. G. et al. (1986) Gastroenterol. 90:350–354.
Bratton, A. C. and Marshall, K. (1939) J. Biol. Chem. 128:537–550.
Karnes, H. T. et al. (1984) Clin. Chem. 30:1565–1567.
Bando, N. et al. (1990) Clin. Chem. 36:1937–1940.
Karnes, H. T. et al. (1985) J. Chromatogr. 338:377–388.
Riley, C. M. (1987) Xenobiotica 17:365–383.
Durie, P. R. et al. (1992) J. Pediatrics 121:413–416.
Berg, J. D. et al. (1986) Clin. Chem. 32:1010–1012.
Braganza, J. M. et al. (1983) Clin. Chim. Acta. 130:339–347.
Puntis, J. W. L. et al. (1988) Arch. Dis. Childhood 63:780–784.
Mitchell, C. J. et al. (1981) Brit. Med. J. 282:1751–1753.
Sterchi, E. E. et al. (1988) Arch. Biochem. Biophys. 265:105–118.
Gyr, K. et al. (1978) Dig. Dis. 23:413–416.
Meyer, B. M. et al. (1987) Pancreas 2:44–47.
Heptner, G. et al. (1989) Gastroenterol. 97:147–153.
Toskes, P. P. (1984) Pharmacother. 4:74–80.
Caspary, W. F. (1986) Gastroenterology, vol. 15 Diarrhoea (G. J. Krejs, ed.), pp. 649–655.
Stradley, R. (1986) J. Lab. Clin. Med. 107:10–14.
Bier, D. M. (1987) Clin. Endocrin. Metab., vol. I, No. 4 (Alberti et al., eds.) pp. 817–836.
Vogel's Textbook of Practical Organic Chemistry, 5th ed., Longman, New York, 1989, pp. 856–857.
Friedman, L. and Schechter, H. (1960) J. Org. Chem. 26:2522–2524.
Vogel's Textbook of Practical Organic Chemistry, 5th ed., Longman, New York, 1989, p. 896.
Murray, III, A. and Williams, D. L. (1958) Organic Synthesis with Isotopes, Interscience, New York, p. 319.
Murray, III, A. and Williams, D. L. (1958) Organic Synthesis with Isotopes, Interscience, New York, pp. 367–368.
Vogel's Textbook of Practical Organic Chemistry, 4th ed., Longman, New York, 1978, p. 684.
Vogel's Textbook of Practical Organic Chemistry, 5th ed., Longman, New York, 1989, p. 919.
C.A. 86–021605/04, Berlin Chemie VEB.
Murray, III, A. and Williams, D. L. (1958) Organic Synthesis with Isotopes, Interscience, New York, pp. 1307–1311.
Nealon, W. H. et al. (1986) Ann. Surg. pp. 430–437.
Tanaka, T. et al. (1988) Surg. Gyn. Obst. 166:200–205.

*Primary Examiner*—James C. Housel
*Assistant Examiner*—Jan M. Ludlow
*Attorney, Agent, or Firm*—Greenlee and Winner

[57] ABSTRACT

A bentiromide test for evaluation of pancreatic function is provided which includes the steps of administering a stable, non-radioactive isotope of PABA along with the bentiromide and measuring the natural PABA and PABA isotope by gas chromatography mass spectroscopy (GC/MS). In a preferred embodiment, xylose is also administered and measured in the sample by GC/MS.

11 Claims, 4 Drawing Sheets

NON-INVASIVE EVALUATION OF MALDIGESTION AND MALABORPTION

This is a continuation of application Ser. No. 08/053,545, filed on Apr. 15, 1993 now abandoned.

FIELD OF THE INVENTION

Medical diagnostic tests in the field of gastroenterology are provided, specifically tests of pancreatic and small bowel function, comprising the administration of stable, non-radioactive isotopes of substances measured using gas chromatography mass spectroscopy.

BACKGROUND OF THE INVENTION

There are a number of patients who are on pancreatic supplements for unclear reasons or for whom the proper dose is unknown. The dose can range from three capsules per day to 24 capsules per day at a cost of approximately $0.30 per capsule. Due to actual or perceived difficulty with current testing methods, when physicians suspect pancreatic insufficiency, they will empirically place patients on different amounts of pancreatic enzyme and, if the patients fail to gain weight or their symptoms are not controlled, they arbitrarily increase the amount of enzyme, often without any confirmatory evidence that the patient's symptoms are due to pancreatic insufficiency. Abdominal pain, weight loss and diarrhea are very common symptoms of many different ailments that have nothing to do with small intestinal malabsorption or pancreatic dysfunction. One of the most often-used tests for pancreatic dysfunction is the bentiromide test. This test leads to misdiagnosis in at least twenty percent of cases. (Chymex package insert, Adria Laboratories, 1988, incorporated herein by reference, and data presented herein.) Because of its low sensitivity, the bentiromide test has been useful only for confirmation of severe pancreatic dysfunction (E. P. DiMagno (1982), "Diagnosis of Chronic Pancreatitis: Are Non-Invasive Tests of Exocrine Pancreatic function Sensitive and Specific?" (editorial), Gastroenterol. 83:143–146).

The standard bentiromide test for pancreatic insufficiency is a test which is often used because it does not require patient intubation or expensive endoscopy. Bentiromide (brand name Chymex) is a diagnostic agent marketed by Adria Laboratories, Columbus, Ohio. Its chemical formula is N-benzoyl-L-tyrosyl-p-aminobenzoic acid. This compound, together with analogous compounds also suitable for use in testing pancreatic functioning, is described in De Benneville U.S. Pat. No. 3,893,992 issued Jul. 8, 1975, incorporated herein by reference.

Bentiromide consists of a para-aminobenzoic acid (PABA) moiety attached to a synthetic peptide by a chymotrypsin-labile bond. Chymotrypsin is a pancreatic exocrine enzyme widely held to be the first enzyme to have decreased output with developing pancreatic insufficiency. Bentiromide is typically administered to a fasting patient in 500 mg. amounts. The patient is then encouraged to drink large amounts of water, and urine is collected over the following six hours. Measurement of excretion of the PABA portion of the bentiromide is then measured by a 1939 assay for arylamines modified in 1945. (Chymex package insert, Adria Laboratories, 1988).

The assay for arylamines is quite nonspecific, as there are numerous arylamines in urine and serum. If the test gives a low value suggesting pancreatic exocrine insufficiency, the possibility of problems in PABA absorption and excretion must be ruled out (C. Lang, et al., "Assessment of exocrine pancreatic function by oral administration of N-benzoyl-L-tyrosyl-p-aminobenzoic acid (Bentiromide): 5 years' clinical experience" (1981) Br. J. Surg. 68:771–775), and the patient is then required to return in about a week to repeat the procedure with PABA only (C. J. Mitchell, et al. (1979), "Improved Diagnostic Accuracy of a Modified Oral Pancreatic Function Test," Scand. J. Gastroenterol 14:737–741; Z. Weizman, et al. (1985), "Bentiromide Test for Assessing Pancreatic Dysfunction Using Analysis of Para-Aminobenzoic Acid in Plasma and Urine," Gastroenterology 89:596–604; V. S. Hubbard, et al. (1984), "Diagnostic and Therapeutic Applications of Bentiromide Screening Test for Exocrine Pancreatic Insufficiency in Patients with Cystic Fibrosis," Dig. Dis. and Sci. 29:881–889). The second procedure is used to correct for factors such as difficulties in absorption and excretion of PABA which can affect the amount of PABA present in the urine or serum.

The standard bentiromide test as applied to urine is inconvenient and often inaccurate because of the required six-hour urine collection, interference by common medications, and alterations in gastric emptying and renal function. Potential inaccuracies also occur because the assay is not specific for PABA. The above difficulties may account for the greater than twenty percent overlap between normals (range 50–90% recovery) and those with pancreatic disease (range 10–70% recovery); this is a significant problem.

The bentiromide test is useful to diagnose pancreatic insufficiency in children. A modified dose of 0.015 g/kg body weight has been used, and PABA recovery measured in faeces. (M. Sacher, et al. (1978), "PABA screening test for exocrine pancreatic function in infants and children," Arch. Dis. in Childhood 53:639–641). The bentiromide and xylose tests are described in attempts to evaluate pancreatic function and malabsorption in cats (E. C. Hawkins, et al. (1986), "Digestion of bentiromide and absorption of xylose in healthy cats and absorption of xylose in cats with infiltrative intestinal disease," Am. J. Vet. 47:567–569). Pancreatic insufficiency is correlated with cystic fibrosis. (S. Nousia-Arvanitakis, et al. (1978) "Diagnosis of exocrine pancreatic insufficiency in cystic fibrosis by the synthetic peptide N-benzoyl-L-tyrosyl-p-aminobenzoic acid," J. Pediatrics 92:734–737.) Some investigators have attempted to make the bentiromide test more sensitive by measuring PABA in serum rather than urine at different time points after ingestion of bentiromide. (S. A. Gharbo, et al. (1985), "Colorimetric Plasma Assay for the Bentiromide Test (BT-PABA) for Exocrine Pancreatic Insufficiency," Anal Biochem. 148:228–232; Z. Weizman, et al. (1985), "Bentiromide Test for Assessing Pancreatic Dysfunction Using Analysis of Para-Aminobenzoic Acid in Plasma and Urine," Gastroenterology 89:596–604; D. Laufer, et al. (1991), "The Bentiromide Test Using Plasma p-Aminobenzoic Acid for Diagnosing Pancreatic Insufficiency in Young Children," Gastroenterol. 101:207–213) Cystic fibrosis patients test abnormally low using the plasma bentiromide test. Measurement at 90 minutes post-administration is recommended to minimize error (G. Koren, et al. (1985), "Altered PABA Pharmacokinetics in Cystic Fibrosis," Dig. Dis. & Sci. 30:928–932; P. G. Lankisch, et al. (1986) "Pancreolauryl and NBT-PABA Tests, Are Serum Tests More Practicable Alternatives to Urine Tests in the Diagnosis of Exocrine Pancreatic Insufficiency?", Gastroenterol. 90:350–354).

The serum samples are generally analyzed for total arylamines by the Bratton-Marshall Reaction. (Bratton, A. C. and Marshall, K., "A new coupling component for sulfanilamide and other aromatic acids in dog and man," J. Biol.

Chem. 128:537–550), although additional analytical tests have been proposed (H. T. Karnes, et al. (1984), "Determination of p-Aminobenzoic Acid in Urine by Room-Temperature Phosphorimetry, with Application to the Bentiromide Test for Pancreatic Function" Clin. Chem. 30:1565–1567; N. Bando, et al. (1990) "Enzymatic Method for Selective Determination of 4-Aminobenzoic Acid in Urine," Clin. Chem. 36:1937–1940; C. M. Riley, et al. (1985) "Analysis of N-Benzoyl-L-Tyrosyl-p-Aminobenzoic Acid (Bentiromide) Metabolites in Urine by Ion-Pair High-Performance Liquid Chromatography," J. Chromatography 338:377–388; C. M. Riley (1987) "Selected aspects of the development of methods for the analysis of drugs by high performance liquid chromatography," Xenobiotica 17:365–383; P. R. Durie, et al. (1992), "Bentiromide test using liquid chromatographic measurement of p-aminobenzoic acid and its metabolites for diagnosing pancreatic insufficiency in childhood," J. Pediatrics 121:413–416).

Another expedient for making the bentiromide test more sensitive is to stress the pancreas with additional protein (J. D. Berg, et al. (1986), "Exocrine Pancreatic Function as Determined in a Same-Day Test with Use of Bentiromide and p-Aminosalicylic Acid," Clin. Chem. 32:1010–1012; J. M. Braganza, et al. (1983), "Observations on the BT PABA/$^{14}$C-PABA tubeless test of pancreatic function," Clinica Chimica Acta, 130:339–347).

To solve the problem of having the patient return a week later for a separate PABA control test, it has been proposed to administer p-aminosalicylic acid with the bentiromide since its metabolism closely tracks that of PABA (J. D. Berg, et al. (1986), "Exocrine Pancreatic Function as Determined in a Same-Day Test with Use of Bentiromide and p-Aminosalicylic Acid," Clin. Chem. 32:1010–1012; J. W. L. Puntis, et al. (1988), "Simplified oral pancreatic function test," Arch. Dis. in Childhood 63:780–784). It has also been proposed to administer a radioactive isotope of PABA simultaneously with the bentiromide (J. M. Braganza, et al. (1983), "Observations on the BT PABA/$^{14}$C-PABA tubeless test of pancreatic function," Clinica Chimica Acta, 130:339–347); C. J. Mitchell, et al. (1981) "Preliminary evaluation of a single-day tubeless test of pancreatic function," Brit. Med. J. 282:1751–1753). Another test known to the art for measuring pancreatic insufficiency involves the use of radioactive isotopes of Vitamin $B_{12}$ (U.S. Pat. No. 4,279,886 issued Jul. 21, 1981 to Robert H. Allen). However, these tests require administration of undesirable radioactive materials. Such radioactive materials cannot be administered in amounts stoichiometrically equivalent to the administered bentiromide, thus the sensitivity of the test is not as high as would be desirable.

Conversion of bentiromide to PABA by enzymes other than chymotrypsin does occur, but only in residual amounts (E. E. Sterchi, et al. (1988), "N-Benzoyl-L-tyrosyl-p-aminobenzoic Acid Hydrolase: A Metalloendopeptidase of the Human Intestinal Microvillus Membrane Which Degrades Biologically Active Peptides," Arch. Biochem. & Biophys. 265:105–118). Common intestinal bacteria also do not appear to convert bentiromide to PABA (K. Gyr, et al. (1978), "Chymotrypsinlike Activity of Some Intestinal Bacteria," Dig. Dis. 23:413–416). Thus, false negative results for pancreatic insufficiency with this test due to other sources of PABA derived from the administered bentiromide do not present a problem. It is, of course, necessary that other dietary sources of PABA be ruled out.

Patients with severe small bowel disease may have symptoms similar to those of patients with pancreatic insufficiency—diarrhea, steatorrhea or weight loss. Since PABA must be absorbed through the small intestine and partially conjugated by the liver, theoretically tests in patients with small bowel or liver disease could produce false positive results, i.e., decreased serum PABA after oral administration of bentiromide without pancreatic disease being present. The bentiromide test is generally believed to be reliably confirmatory of pancreatic insufficiency despite the possibility that abnormal results could occur in patients with small bowel disorders or liver disease (B. M. Meyer, et al. (1987), "Bentiromide Test Is Not Affected in Patients with Small Bowel Disease or Liver Disease," Pancreas 2:44–47), although the test does not show good specificity in gastrectomized patients (G. Heptner, et al. (1989), "Exocrine Pancreatic Function after Gastrectomy," Gastroenterol. 97:147–153). Liver disease does not interfere with the results until the disease is quite severe, the patient obviously jaundiced and not likely to be administered bentiromide. False positives due to small bowel disease may be readily detected using urinary absorption tests such as the xylose test or small bowel x-rays (P. P. Toskes (1984), "The Bentiromide Test for Pancreatic Exocrine Insufficiency," Pharmacother 4:74–80).

The serum xylose test is one of the best non-invasive methods for diagnosing intestinal malabsorption. In this test, D-xylose, a five-carbon sugar not naturally present in the body or in foodstuffs, is given orally and an estimation of the increase in serum xylose content is carried out through colorimetric determination (CD) of non-glucose reducing sugars in serum. However, the test is occasionally misleading by giving both false positive and false negative results. Older xylose tests measured xylose in the urine. Problems with this test include the fact that the Roe and Rice method of D-xylose analysis is non-specific and cross-reacts partially with glucose. Hence, this method is not accurate in the presence of hyperglycemia and glycosuria. Furthermore, the test critically depends on complete emptying of the urinary bladder at five hours and on intact renal function. False positive results are frequently obtained with both the serum and urine tests in patients with intestinal bacterial overgrowth (W. F. Caspary, "Diarrhoea and Carbohydrate Malabsorption," (1986) in Clinics in Gastroenterology, Vol. 15 Diarrhoea (G. J. Krejs, ed.) at 649–650 (W. B. Saunders Company, London, Phila., Toronto)), but delays in gastric emptying do not appear to affect the results (R. Stradley (1986), "Gastric absorption of D-xylose in the rat: its influence on the D-xylose absorption test," J. Lab. Clin. Med. 107:10–14).

An algorithm for evaluating further procedures using the bentiromide and xylose tests in patients with symptomatic diarrhea, steatorrhea or weight loss useful for diagnosing and assessing the necessity for further testing is presented in P. P. Toskes (1984), "The Bentiromide Test for Pancreatic Exocrine Insufficiency," Pharmacother. 4:74–80, incorporated herein by reference. Abnormal bentiromide with normal xylose indicates pancreatic exocrine insufficiency. If both tests are abnormal, primary small bowel disease is suggested, and a small bowel biopsy should be performed. Normal bentiromide with abnormal xylose indicates bacterial overgrowth and a $^{14}$C-xylose breath test and small bowel culture are indicated. If both tests are normal, the article states, pancreatic and small bowel disease are not ruled out, and further tests, such as the $^{14}$C-xylose breath test, small bowel culture, small bowel biopsy and secretin tests are indicated.

Stable isotopes have been used in metabolic investigations such as measurement of body water composition and energy expenditure and studies of substrate fuel metabolism in pregnancy, infants and adults (D. M. Bier (1987), "The use of stable isotopes in metabolic investigation", in Clinical Endocrinology and Metabolism, Vol I, No. 4 (Alberti et al., eds.) 817–836). Stable isotopes of PABA have not been previously known to the art.

SUMMARY OF THE INVENTION

Figure 1:
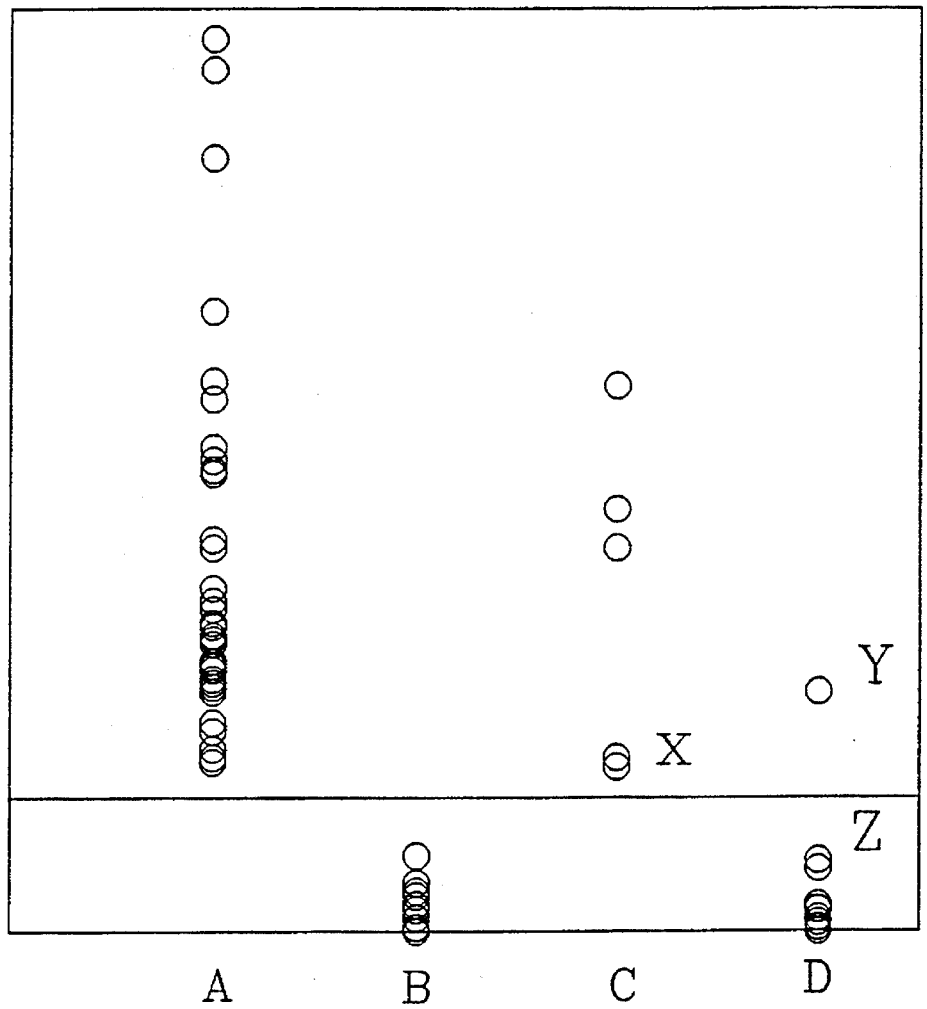
FIG. 1 shows the ratio of labelled PABA to natural PABA in sera sixty minutes after administration of the bentiromide test of this invention to four groups of patients designated A, B, C and D. A=Normal; B=Previously diagnosed pancreatic insufficiency with cystic fibrosis; C=Symptoms of pancreatic insufficiency but failed to respond to pancreatic supplements; D=Symptoms of pancreatic insufficiency and responded to pancreatic supplements.

The present invention provides an improvement in the bentiromide test for assessing pancreatic insufficiency. Bentiromide (N-benzoyl-L-tyrosyl-p-aminobenzoic acid) has the following structure:

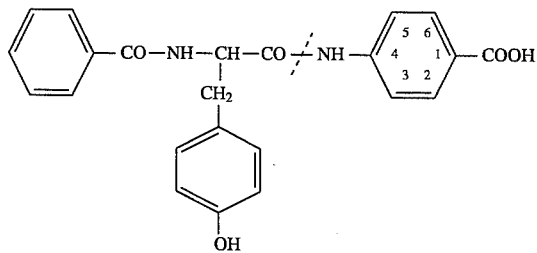

The pancreatic enzyme chymotrypsin cleaves the N-benzoyl-L-tyrosine moiety from the molecule at the dotted line to leave para-aminobenzoic acid (PABA) which can be measured in serum or urine. Low values of PABA are indicative of pancreatic insufficiency.

It is desirable to avoid the disadvantages of having patients collect urine for six hours and then return after a week for a control test involving the administration of PABA with another six-hour urine collection, as in previously-described bentiromide tests. The second test is not only inconvenient, but it also introduces possible error due to the fact that PABA metabolism may have fluctuated over the period of time between tests or arylamines such as Tylenol may have been consumed. It is further desirable to avoid the administration of radioactive isotopes of PABA, both because radioactive materials are harmful to the body, and because such radioactive isotopes cannot be administered in amounts stoichiometrically equivalent to the bentiromide. It is therefore an object of this invention to provide a same-day bentiromide test which does not involve the administration of radioactive PABA isotopes.

It is further desirable to administer a test of small bowel absorption simultaneously with the bentiromide test, which is both more sensitive and more accurate than prior xylose tests, in that it uses a more accurate analytical test for the presence of xylose in body fluids and does not require complete bladder emptying which is difficult to ensure.

It is further desirable to decrease the amount of bentiromide which must be administered to the patient, as well as the amount of PABA control, and to increase the sensitivity of both tests by providing a more accurate analytical method.

Since many common substances including sun creams and vitamins contain PABA (Chymex package insert, Adria Laboratories, 1988), it is difficult to ensure that PABA from these sources does not interfere with the test results. Thus, it is desirable to provide a test in which such outside sources of PABA cannot interfere with the results or can be corrected for.

Accordingly, improved methods for evaluating pancreatic insufficiency and small bowel malabsorption are provided. The bentiromide-xylose test of this invention has changed the diagnosis of approximately twenty percent of patients who were previously diagnosed as having small bowel malabsorption, or having pancreatic insufficiency. Proper diagnosis is essential to avoid more invasive and expensive procedures such as small bowel biopsy or the administration of pancreatic enzymes.

The methods of this invention are useful for both human and veterinary patients such as cats, dogs, rodents, cows, horses, and other mammals.

In one embodiment, the method of this invention for evaluating causes of maldigestion and malabsorption in a patient comprises:

a) obtaining a first 0-time fluid sample from the patient and measuring PABA concentration therein;

b) administering to said patient a known quantity of bentiromide, preferably between about 6 mg and about 7 mg, along with a known quantity, preferably about 5 grams of xylose;

c) administering with said bentiromide and xylose a known amount, preferably between about 2.0 mg and 2.5 mg of a non-radioactive isotope of PABA having a molecular weight different from natural PABA;

d) allowing sufficient time, preferably between about one-half hour and about four hours, and more preferably about one hour, for said xylose, bentiromide and PABA isotope to be absorbed through the patient's digestive tract and pass into said fluid;

e) obtaining a second fluid sample, preferably serum, from said patient, and measuring the xylose, natural PABA, and PABA isotope therein, preferably using gas chromatography mass spectroscopy;

f) comparing said measured amounts and administered amounts to determine the proportion of administered bentiromide converted to natural PABA in the patient's body, said proportion being diagnostic of pancreatic function, and to determine the proportion of xylose absorbed in the digestive tract, said proportion being diagnostic of small bowel disease or bacterial overgrowth.

It is preferred that the bentiromide test of this invention be administered after overnight fasting except for coffee and water. The term "0-time" means the time before the bentiromide is administered, or within about 30 minutes before administration.

The amount of bentiromide administered may be any known amount safely tolerated by the patient which can result in measurable amounts of natural PABA in the urine or serum given normal pancreatic function. In general, administered amounts of bentiromide from about 1 mg to 1 g are useful in this invention, and preferably about 6 to about 7 mg are used. The process of this invention which measures PABA rather than non-specific aryl amines, preferably by GC/MS, allows the amount of administered bentiromide to be reduced many-fold over amounts used in previously-described bentiromide tests. The PABA isotope is preferably administered in stoichiometrically equivalent amounts to the amount of bentiromide administered. It is desired to minimize the amount of PABA isotope given due to the expense of the isotope and because it is not a normal food substance, although no harmful effects of larger quantities are known or believed to occur. However, sufficient PABA isotope must be given to be detectable over background in serum or urine. Amounts of PABA isotope from about 500 μg to about 300 mg are useful in this invention, and preferably between about 2 and about 2.5 mg, is used.

Because of the small quantities of bentiromide and PABA isotope given in the preferred embodiments of this invention, pancreatic enzyme output is stimulated and the enzymes put out by the pancreas are saturated by co-administering a test meal of another protein, preferably 8 fluid ounces Resource (Sandoz Nutrition, Minneapolis, Minn.), a lactose-free protein containing 8.8 grams of protein as well as physiologic quantities of carbohydrate, fats, vitamins which do not contain PABA and minerals.

The PABA obtained in the second fluid sample has been conjugated by the liver to PABA-glucuronide. It is isolated from the second fluid sample and preferably hydrolyzed to remove the glucuronide group, then derivatized, preferably with N-methyl-N-t-butyldimethylsilyltrifluoroacetamide ("t-butyl") for detection by gas chromatography mass spectroscopy (GC/MS). Said t-butyl derivatization is preferred over other known derivatizations known to the art in preparing compounds for GC/MS because atmospheric moisture interferes less with the t-butyl derivative. However, because the t-butyl derivatizing agent which is present in excess amounts forms an interfering peak with the derivatized PABA isotopes at the same retention time, it is necessary to shift the retention times of the PABA and PABA isotopes, preferably by treatment with an anhydride such as propionic, acetic or other anhydride, to form derivative compounds with shifted retention times.

The PABA isotope is preferably a non-radioactive stable isotope, having a molecular weight different from natural PABA, such as a carbon 13, nitrogen 15, or deuterium isotope, preferably an isotope having a molecular weight at least two mass units greater than natural PABA, and most preferably is $[^{13}C]_6$-PABA (custom-synthesized by C/D/N Isotopes, Quebec, Canada) in which all six carbons of the phenyl ring are labelled. Stable isotopes having molecular weights differing from the natural compound by x mass units may be designated herein by the term $PABA^{m+x}$ where x is an integer from 1–18, and such isotopes may be made using any combination of labelled elements as set forth above to reach the required mass. Natural PABA has a molecular weight of 137. The stable PABA isotopes useful herein thus have molecular weights from 138 to 154.

The xylose is used to test small bowel function. Xylose is a substance not naturally present in the body. D-xylose is available commercially from Adria Labs, Columbus, Ohio, and Sigma Chemicals, St. Louis, Mo. The amount of xylose administered is not critical, but is preferably about 5 g.

Preferably, a second isotope of PABA having a molecular weight different from the first isotope and from natural PABA is added to the sample prior to GC/MS measurement as an internal standard for the measurements. The use of such internal standards is known to the art. Preferably, the second PABA isotope differs by at least two mass units from both natural PABA and the first PABA isotope and also differs from xylose and its stable isotopes by at least two mass units. Most preferably, it is 2,6-$[^2H]_2$-PABA (available by custom synthesis from C/D/N Isotopes, Quebec, Canada).

An isotope of xylose, preferably $[^{13}C]_1$-xylose (C/D/N Isotopes, Quebec, Canada; ICN Pharmaceuticals, Irvine, Calif.) is used similarly as an internal standard to quantitate xylose in the GC/MS measurement.

It will be appreciated by those skilled in the art that measurement need not be limited to GC/MS but can be performed by any method providing the requisite accuracy and sensitivity.

In another embodiment of this invention, the bentiromide test of pancreatic function comprises:
 a) obtaining a first 0-time fluid sample, preferably serum, from the patient and measuring PABA concentration therein;
 b) administering to said patient a known quantity of bentiromide;
 c) administering with said bentiromide a non-radioactive isotope of PABA having a molecular weight different from natural PABA;
 d) allowing sufficient time, preferably between about one-half hour and about four hours, preferably about one hour, for said bentiromide and PABA isotope to be absorbed through the patient's digestive tract and pass into said fluid;
 e) obtaining a second sample of the same fluid taken in step (a) from said patient, and measuring the natural PABA and isotope PABA therein, preferably by gas chromatography mass spectroscopy;
 f) comparing said measured amounts and administered amounts to determine the proportion of administered bentiromide converted to natural PABA in the patient's body, said proportion being diagnostic of pancreatic function.

The need for taking a 0-time sample is obviated, and errors resulting from problems in tracking PABA metabolism and possible extraneous sources of PABA are avoided, by utilizing a further embodiment of the invention involving the administration of a stable isotope of bentiromide labelled on the PABA moiety thereof, the simultaneous administration of a second stable PABA isotope having a mass different from the PABA portion of the administered bentiromide isotope, and the use of a third stable PABA isotope having a mass different from the first and second PABA isotopes used as a quantitation standard for GC/MS. The method comprises:
 a) administering to said patient a known quantity, preferably between about 6 mg and about 7 mg, of a non-radioactive isotope of bentiromide having a molecular weight different (preferably by at least two mass units) from natural bentiromide, wherein said isotope is labelled on the PABA portion thereof and is capable of being cleaved by pancreatic enzymes to a first PABA isotope;
 b) administering with said bentiromide isotope a second non-radioactive isotope of PABA having a molecular weight different (preferably by at least two mass units) from both natural PABA and said first PABA isotope;

c) allowing sufficient time for said bentiromide isotope to be processed in, and said PABA isotopes to be absorbed through, the patient's digestive tract;

d) obtaining a fluid sample from said patient, preferably serum, and measuring the PABA isotopes therein, preferably by GC/MS.

e) comparing said measured amounts and administered amount to determine the proportion of administered bentiromide isotope converted to the first PABA isotope in the patient's body relative to the measured amount of the PABA isotope which was administered, said proportion being diagnostic of pancreatic function.

In a preferred embodiment, a third isotope of PABA having a molecular weight different from said administered isotopes of PABA (preferably by at least two mass units) is added to said fluid sample prior to said measurement to provide a standard for said measurement.

The isotope of bentiromide administered to the patient may be any stable, non-radioactive isotope having a molecular weight different from bentiromide and labelled on the PABA portion of the molecule, such as a carbon 13, nitrogen 15, or deuterium isotope, and preferably is N-benzoyl-L-tyrosyl-2,6-$[^2H]_2$-PABA. The administered PABA isotope may be any isotope as listed above other than the PABA isotope cleaved from the bentiromide isotope, and is preferably $[^{15}N]$-$\alpha[^{13}C]$-2,6-$[^2H]_2$-PABA.

The isotope used as a measurement standard for the bentiromide test may be any of the above isotopes other than the one administered, and preferably is $[^{13}C]_6$-PABA or a stable PABA isotope of the same mass.

As set forth above, a test of small bowel function may be included with the test using an isotope of bentiromide, e.g. xylose may be administered with the isotopes of bentiromide and PABA and all substances measured in the fluid sample.

This invention also provides stable isotopes of PABA and bentiromide as new compositions of matter. The preferred $[^{13}C]$ isotopes of PABA as set forth above, including the preferred $[^{13}C]_6$ isotope (M+6), are synthesized by a procedure comprising nitration of commercially available $[^{13}C]$-bromobenzene and separation of isomers followed by substitution of the bromide with cuprous cyanide, hydrolysis of the nitrile under acidic or basic conditions, and reduction of the nitro group to an amine. The preferred deuterium isotope, 2,6-$[^2H]_2$-PABA (M+2), is prepared by exchanging 4-nitroaniline as its hydrochloride salt in deuterium oxide and transforming to 4-nitrobenzonitrile-2,6-$[^2H]_2$ via a Sandmeyer reaction with alkali cyanides. The latter product is then converted to 2,6-$[^2H]_2$-PABA as described above for $^{13}C$-PABA. Alternatively, $[^{13}C]$-PABA may be prepared from commercially available $[^{13}C]$-aniline by acetylation of the amine, followed by nitration of the ring and hydrolysis of the amide in deuterochloric acid to produce 4-nitroaniline-$[^{13}C]$-N,N-2,6-$[^2H]$deuterochloride-deuterochloride which is converted into $[^{13}C]$-PABA through the nitrile as described above. The preferred isotope, $\alpha$-$[^{13}C]$-$[^{15}N]$-2,6-$[^2H]_2$-PABA (M+4), is prepared by the same process, substituting nitric $[^{15}N]$ acid for natural nitric acid in the nitration step and substituting cyanide-$[^{13}C]$ for natural cyanide in the Sandemeyer reaction.

Additional PABA isotopes are prepared by analogous methods as described herein.

The preferred isotopes of bentiromide may be synthesized from the PABA isotopes provided herein by means known to the art, e.g. the method of De Benneville U.S. Pat. No. 3,893,992 issued Jul. 8, 1975 (Example 9).

Also provided herein is a method of diagnosing small bowel dysfunction comprising administering to a patient a known quantity of a substance not naturally present in the body which is absorbed in the small bowel (such as xylose as described above), allowing sufficient time for said substance to be absorbed through said patient's digestive tract, and measuring the quantity of said substance in a fluid sample, preferably serum, taken from said patient by gas chromatography mass spectroscopy.

DETAILED DESCRIPTION OF THE PREFERRED EMBODIMENTS

Improved methods are provided for evaluating the causes of maldigestion and malabsorption in a patient. The bentiromide test described above is modified by the methods of this invention to provide improved accuracy, sensitivity, and convenience of administration for both doctor and patient.

A first 0-time fluid sample is obtained from the patient and para-aminobenzoic acid (PABA) concentration is measured therein to determine background PABA concentrations in the patient. As there are many sources of PABA, such as vitamins or other drugs the patient may be taking, this figure can be used as a correction figure when PABA is later measured in the fluid. The fluid can be urine or serum, preferably serum.

A known quantity of N-benzoyl-L-tyrosyl-p-aminobenzoic acid (bentiromide) is orally administered to the patient, also at 0-time. Preferably, the amount of bentiromide is much less than that administered in prior art bentiromide tests, i.e., no more than about 7 mg.

It will be understood by those skilled in the art that bentiromide analogs such as those described in De Benneville U.S. Pat. No. 3,893,992 issued Jul. 8, 1975, are equivalent to bentiromide and may be substituted therefor in this invention with measurement of the cleaved product in a manner analogous to the methods described herein.

Because of the small amount of bentiromide administered, it is desirable to co-administer a larger amount of a protein such as casein, dipeptides or polypeptides, with aromatic amino acids as part of the structure, e.g. Ensure, Ross Laboratories, Columbus, Ohio, or Resource, Sandoz Nutrition, Minneapolis, Minn., to stress the pancreas, saturate the pancreatic enzymes, and make the test more sensitive. Preferably, the protein is administered in an amount between about 8 grams and about 9 grams, and most preferably 250 ml of Resource is administered.

In a preferred embodiment, a known quantity of xylose is also administered at 0-time to test for problems in small bowel absorption which might interfere with the results of the bentiromide assay. Xylose was found to be detectable by GC/MS without interfering with the quantitation of PABA from bentiromide, administered stable isotope PABA or stable isotope PABA used to standardize the assay.

Also at 0-time, a known amount of a non-radioactive, stable isotope of PABA having a molecular weight different from natural PABA is administered to the patient. Preferably, PABA is administered in a stoichiometrically equivalent amount to the amount of bentiromide administered. The PABA isotope should differ from natural PABA by at least two mass units.

The preferred isotope is $[^{13}C]_6$-PABA in which all six carbons of the phenyl ring are labelled, obtained by custom synthesis from C/D/N Isotopes, Quebec Canada.

Sufficient time for said xylose, bentiromide and PABA isotope to be absorbed through the patient's digestive tract and pass into the urine or serum is then allowed. The amount of time can be between about one-half hour and about four hours and is preferably about one hour.

A second fluid sample is then obtained from said patient (urine if the first sample was a urine sample and serum if the first sample was a serum sample), preferably serum.

The xylose, natural PABA and PABA isotope in the sample are then measured using gas chromatography mass spectroscopy. PABA is present in the fluid in the conjugated form of PABA-glucuronide; however, PABA-glucuronide is difficult to purify from urine or serum by the usual procedures. The molecule cyclizes at neutral pH. Therefore it is necessary to hydrolyze the glucuronide prior to final analysis. Also, prior to GC/MS, the purified PABA isotope must be derivatized with N-methyl-N-t-butyldimethylsilyltrifluoroacetamide ("t-butyl") or other stable derivatizing agents that result in a volatile (on GC) derivative for gas chromatography.

Derivatization with "t-butyl" is preferred because the derivative is more stable to atmospheric moisture than derivatives made with other known derivatizing agents. However, as set forth above, the "t-butyl" which is present in excess amounts forms a peak which interferes with the "t-butyl" PABA and "t-butyl" PABA isotopes unless these are further modified to change their retention times and molecular weights, preferably with an anhydride such as acetic or propionic anhydride.

In a preferred embodiment, a second isotope of PABA is added to both the 0-time and the second fluid sample for standardization. This isotope should have a molecular weight different from both natural PABA and from the first isotope. Preferably, this second isotope is a non-radioactive stable isotope which is stable deuterium, carbon, nitrogen or oxygen-labelled and has a molecular weight at least two mass units different from natural PABA or the first isotope. More preferably this isotope is 2,6-[$^2$H]$_2$-PABA of C/D/N Isotopes, Quebec, Canada. The 2,6-deuterium isotope is sufficiently stable for purposes of this invention; however, the 3,5 isotope is unstable and not suitable for use herein.

Xylose is purified for detection by GC/MS by the process shown in Example 7. The purification process involves rapid deproteination and two-hour derivatization. The analysis involves the examination of one specific ion (M/Z 417) of one specific anomeric peak. Because of natural anomers and possibly incomplete derivatization of carbohydrates, xylose may show several peaks on GC/MS. It is necessary to use a peak providing a linear assay. In the present assay, using a ten-meter column, xylose elutes at 6.6 minutes when the temperature is ramped from 80°–300° C. using helium gas at a head pressure of 50 psi. A second smaller peak elutes at 6.7 minutes. In the method of this invention four peaks are seen, and it has been discovered that monitoring for ion M/Z 417 which occurs at 6.6 minutes provides a linear assay.

A xylose isotope, preferably $^{13}$C$_1$-xylose is used as a standard for quantitation. The ion M/Z 418 having a retention time of 6.6 minutes is used for calibration of the column.

The data collected is then compared to determine the proportion of administered bentiromide converted to natural PABA in the patient's body, said proportion being diagnostic of pancreatic dysfunction, and to determine the proportion of xylose absorbed in the digestive tract, said proportion being diagnostic of small bowel disease.

The abundance of PABA and PABA isotope of the type administered to the patient in the 0-time sample is determined and compared to the abundance of PABA (from cleavage of bentiromide) and isotope PABA in the second sample. After adjustment for differences in the abundance of the identical quantities of PABA isotope used for standardization placed in the assay, the value of PABA in the 0-time sample is subtracted from the abundance of the PABA in the second sample (a like correction is also applied to the PABA isotope of the type administered) and a ratio of natural PABA to PABA isotope of the type administered is then determined. Individuals with a ratio greater than 0.32 are considered normal, individuals with a ratio of 0.28–0.32 are considered indeterminate, individuals with a ratio of less than 0.28 are considered abnormal. It should be emphasized that in the study of patients with documented pancreatic insufficiency to this point, 60-minute samples have not had a ratio of more than 0.18.

The xylose is also measured in the second fluid sample by GC/MS. A value greater than about 2.5 mg/dl is considered normal. A value less than or equal to about 2.5 mg/dl is read as abnormal. Because the xylose test of this invention is done after consuming a test meal (i.e., bentiromide and a protein such as Resource, rather than after fasting as is the case with previously-described xylose tests), the normal xylose range is significantly lower than that for previously-described xylose tests given to fasting patients.

In addition, the PABA ratio may be compared to the quantity of xylose present in the serum sample. Dumping Syndrome (rapid emptying of the stomach) will lead to disproportionately heightened PABA ratio (natural PABA/PABA isotope) compared to xylose, while delayed emptying leads to low values of PABA ratios and relatively higher xylose values.

After obtaining the results of the bentiromide and small bowel absorption tests, further procedures may be indicated, for example according to the algorithm set forth above from P. P. Toskes (1984), "The Bentiromide Test for Pancreatic Exocrine Insufficiency," Pharmacother. 4:74–80. In view of the increased accuracy and sensitivity of the tests as described herein, however, the Toskes Algorithm may be modified. PABA ratios may be related to xylose levels for diagnosis as discussed above. Further, the need for additional testing may be ruled out by the unambiguous results of the test procedures of this invention. When bacterial overgrowth is a suspected cause of abnormal xylose readings, the xylose test may be repeated after a course of broad-spectrum antibiotics.

In a preferred embodiment, to eliminate the necessity for taking a 0-time PABA sample and to obviate any problem caused by PABA in the digestive tract at 0-time, a non-radioactive stable isotope of bentiromide labelled on the PABA portion of the molecule, preferably N-benzoyl-tyrosyl-2,6-[$^2$H]$_2$-PABA, is orally administered with a PABA isotope preferably [$^{15}$N]-α-[$^{13}$C]-2,6-[$^2$H]$_2$-PABA, labelled differently from the PABA portion of the bentiromide isotope. The isotopes are preferably administered in an amount between about 2 mg and about 7 mg, and preferably between about 6 mg and about 7 mg for labelled bentiromide, and 2–2.5 mg for labelled PABA. The bentiromide isotope, when cleaved, preferably releases a PABA isotope having a mass at least about two mass units greater than natural PABA and differs from the PABA isotope administered to the patient by at least about two mass units. The PABA isotope cleaved from the bentiromide isotope is then isolated and measured relative to the simultaneously administered, differently-labelled PABA isotope, by GC/MS as described above using a third PABA isotope, preferably [$^{13}$C]$_6$-PABA as a standard for quantitation.

Bentiromide isotopes for use in this invention may be prepared by one of ordinary skill in the art using PABA isotopes as described above as the starting material, in a process as described in De Benneville U.S. Pat. No. 3,893,992 issued Jul. 8, 1975 (Example 9). Chymotrypsin cleaves on the carboxyl side of a peptide bond of an aromatic amino acid. Thus it will be appreciated by those skilled in the art that molecules analogous to bentiromide which are so cleaved (such as the compounds disclosed in said U.S. Pat. No. 3,893,992, e.g. N-benzoyl-aromatic amine-PABAs [see Examples 1, 3 and 19] such as PABA derivatives of phenylalanine and tryptophan) are useful substitutes for bentiromide in this invention.

EXAMPLES

Example 1

Combined Xylose-Bentiromide Test

Pancreatic and small bowel function were simultaneously evaluated using a gas chromatographic mass spectrometric (GC/MS) method on serum samples. In this method, xylose absorption was quantitated using $[^{13}C]_1$-xylose, a stable isotope of xylose. Absorption of p-aminobenzoic acid (PABA), released from bentiromide by the action of endogenous chymotrypsin, was compared to the absorption of stable isotope PABA ($^{13}C_6$), administered orally simultaneously with bentiromide. The ratio (Pancreatic Ratio) of bentiromide PABA to stable isotope PABA in 60-minute sera samples was determined and expressed as a fraction and quantitated relative to added $2,6[^2H]_2$-PABA.

Example 2

Change in Diagnosis with Improved Bentiromide-D-Xylose Test

The diagnoses of approximately 20% of patients who were originally diagnosed as normal, or as having small bowel malabsorption or pancreatic insufficiency, have been changed using the improved bentiromide-xylose test of this invention.

A 56 year old male presented with diarrhea and hyperthyroidism and was also noted to have significant steatorrhea (63 g fat/24 hours). The patient was further evaluated with standard serum D-xylose testing, which was abnormal (13 mg/dl, nl 20–40). He underwent endoscopy with small bowel biopsy which revealed normal villi with non-specific mild inflammation. The patient then was given the above GC/MS test. A 0-time 10 ml blood sample was taken; 6.7 mg of bentiromide was administered along with 2.0 mg of stable isotope PABA and 5 g D-xylose, and 8 fl. oz. of Resource. Sixty minutes later, 10 ml of blood was drawn. The sera after clotting was collected and the PABA, $[^{13}C]_6$-PABA and xylose were purified and assayed by GC/MS.

The test showed heightened intestinal absorption (serum xylose=15 mg/dl) but pancreatic insufficiency (Pancreatic Ratio=0.06), nl (greater than 0.32). The patient was placed on Pancrease with marked decrease in stool frequency. A repeat qualitative stool fat was normal and he gained 27 kg (60 lbs) on Pancrease. The GC/MS testing provided the correct assessment and allowed appropriate therapeutic intervention for this complicated individual with steatorrhea. The morbid procedure of small intestine biopsy and the associated risk to life and the expense of this procedure would have been avoided had the new test been performed to begin with.

One patient who had a completely normal bentiromide ratio indicating normal pancreatic function with the testing procedure of this invention had a value of only 23% with the original bentiromide test, which is distinctly low in that assay. This patient felt that he had seen no improvement while on pancreatic supplemental enzymes.

A 63-year-old woman with weight loss was referred to us after spending more than $5,000 on evaluation and $150 per month for empiric pancreatic enzyme testing without improvement. Her test was normal. We stopped her enzymes and instituted therapy for depression. She gained 10% of her body weight and was able to eliminate the monthly expense for enzymes.

A 60-year-old male on long-term federal (via VAH) disability for "ulcer disease" had diarrhea. His doctor started empiric Pancrease. This subject then filed for increased disability for pancreatic insufficiency. He was absolutely normal on our test, and therefore did not need the enzymes ($2.00/day at the federal government's expense) or increased disability compensation since there was no increased disability.

A very complicated subject with diarrhea following gastrectomy and partial pancreatectomy for cancer developed diarrhea on chemotherapy. Empiric enzymes were started. Pancreatic insufficiency was ruled out by our testing. His diarrhea improved off enzymes when his chemotherapy was stopped.

Example 3

Bentiromide Test Using PABA Isotope

At 0-time, a blood sample was taken from all patients in the amount of 10 ml, yielding 4–6 ml of serum, an aliquot of which was analyzed by GC/MS for PABA content.

Bentiromide in the amount of 6.7 mg and stable isotope PABA ($[^{13}C]_6$-PABA) in the amount of 2 mg was administered to normal patients and patients with various pancreatic injuries after Internal Review Board approval. After an overnight fast (nothing by mouth after midnight except water or coffee with cream), a 0-time blood sample was drawn. The patients then drank 8 oz. of Resource followed immediately (within less than five minutes) by the test solution comprising 6.7 mg bentiromide, 2 mg stable isotope PABA, and 5 grams of D-xylose dissolved in 30 cc (1 oz.) of water. Sixty minutes later, 10 mls of blood were drawn and the subjects dismissed.

Serum collected one hour after the test meal was analyzed by GC/MS for the ratio of natural PABA to stable isotope PABA. The simultaneous administration of stable isotope PABA with bentiromide corrects for variations in gastric emptying, intestinal absorption, renal function and interfering substances in serum. Results are shown in Table 1.

TABLE 1

Ratio in % of Natural PABA to Stable Isotope PABA

| | |
|---|---|
| Normals (n = 38) | 80 ± 20 range 34–200% |
| Cystic Fibrosis (n = 16) | 4 ± 3 range 0–11% |
| Alcoholic Pancreatitis (n = 4) | 5 ± 6 range 0–14% |
| Other Pancreatitis (n = 4) | 7 ± 6 range 1–16% |
| Partial Pancreatectomy (n = 2) | 2% and 37% |

This testing procedure, specific for PABA (as opposed to arylamines), provides a convenient, accurate method for determining pancreatic exocrine insufficiency. No overlap between normal and abnormal subjects occurred with this test. This is in dramatic contrast to the current bentiromide test where nearly one-half of patients with documented pancreatic insufficiency had normal test results (see bar graph of Chymex, package insert, Adria Laboratories, 1988).

Example 4

Bentiromide Test

Bentiromide and stable isotope PABA were administered as set forth in Example 2 to four groups of patients designated A, B, C, and D on the X axis of FIG. 1. The ratio of labelled (i.e. stable isotope PABA) to bentiromide PABA in sera at 60 minutes is shown on the Y axis.

Group A are considered to be normal individuals who have never been known to have a history of gastrointestinal disease.

Group B are patients who are thought to have pancreatic insufficiency based on the genetic disease, cystic fibrosis. All of Group B fall well below the 0.32 ratio line in the figure.

Group C are patients who have been thought by physicians to have pancreatic insufficiency because of diarrhea, abdominal pain, or unexplained weight loss, but who failed to improve in the patient's and our independent M.D.'s judgment when put on pancreatic supplementary enzymes. As shown in the graph, this entire Group C is normal. It should be noted that Subject "x" had a partial pancreatectomy and felt his bowel movements may have somewhat improved at times but not at other times. Since his test results were normal, we concluded that he did not have pancreatic dysfunction. His symptoms disappeared when other medications were discontinued despite also stopping his pancreatic supplement. Thus, this patient clearly has normal pancreatic function and, as predicted from our test, his symptoms were not related to pancreatic insufficiency.

Group D are patients who were thought to have pancreatic insufficiency based upon their symptoms of abdominal pain, diarrhea, and weight loss, who improved clinically when they were placed on pancreatic enzyme supplement. The patient with the footnote "y" is an individual who probably has an associated syndrome called "Dumping Syndrome" and is seeking compensation from the VA for pancreatic insufficiency. It should be noted that this individual has been turned down for this compensation on the grounds that there is very little evidence that he has pancreatic insufficiency. He does claim improvement while on pancreatic enzymes. Patient "z" had only abdominal pain that disappeared after initiating Pancrease.

Example 5

GC/MS D-Xylose Test

An isotope dilution assay was developed for serum xylose using GC/MS to compare to the CD of serum xylose from a commercial diagnostic company to see if variations in the analysis itself may be a contributing cause to the misleading clinical results. Since GC/MS analysis relies on both column separation and mass identification, it is more specific for xylose determination than CD.

Figure 2:
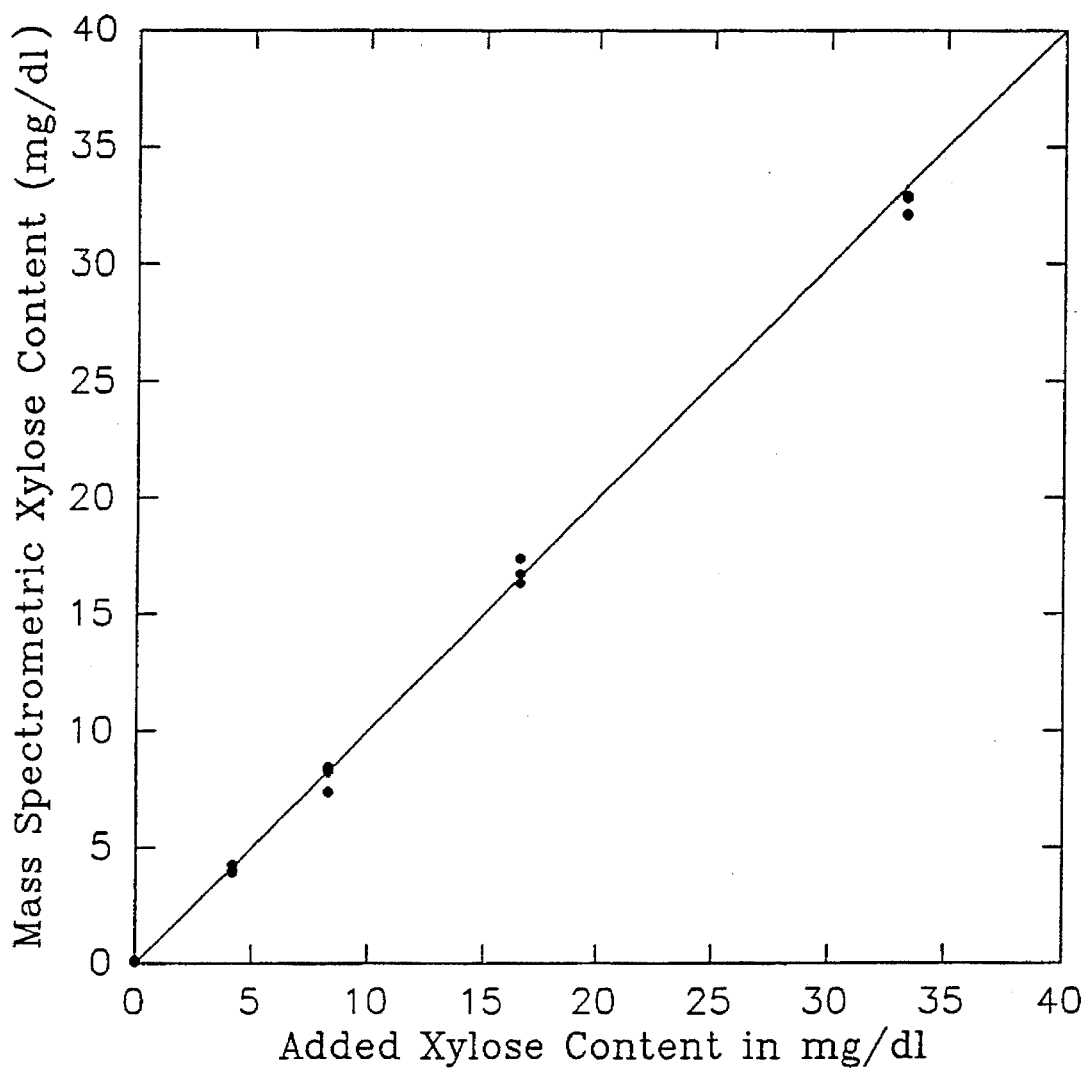
FIG. 2 shows accuracy GC/MS xylose test of this invention to measure known amounts of xylose in samples.
Figure 3:
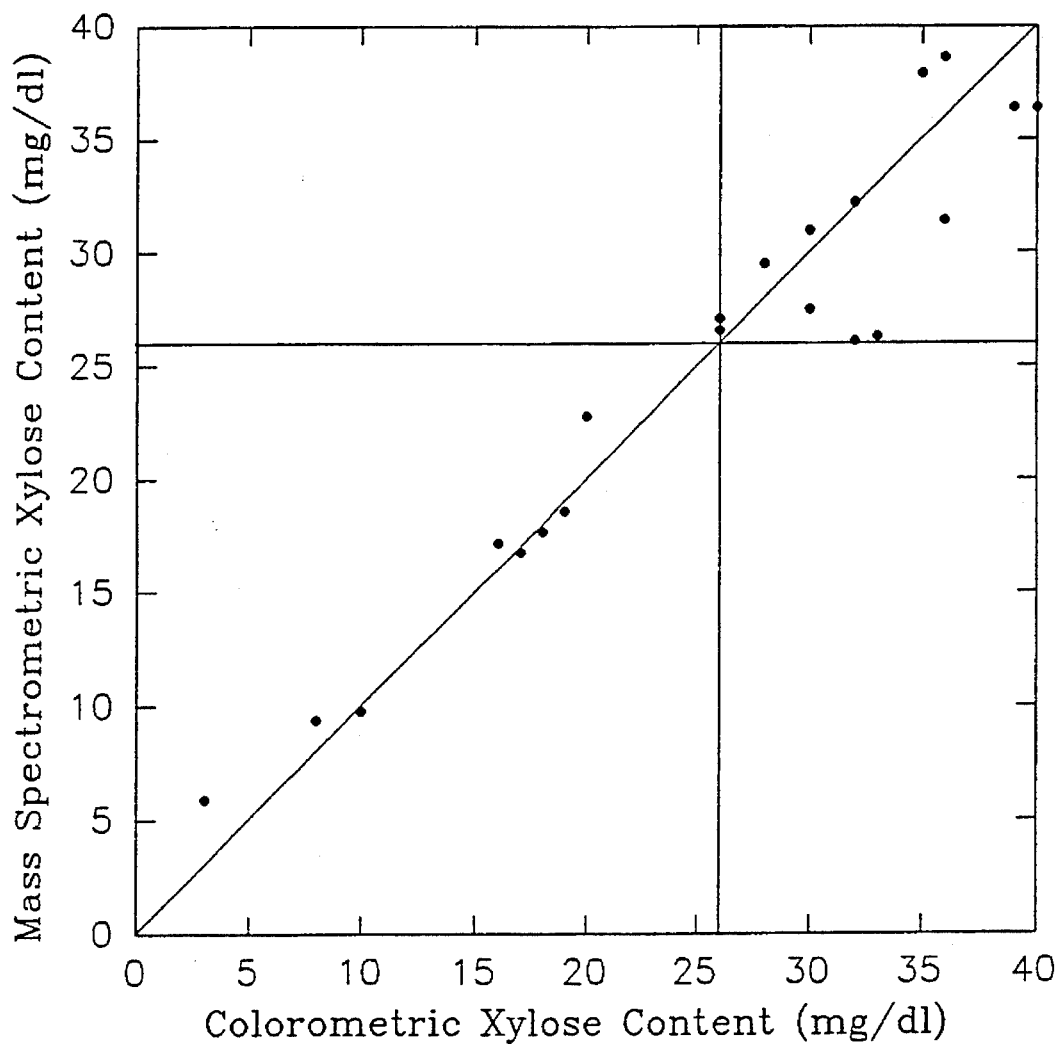
FIG. 3 shows comparison of GC/MS xylose test of this invention with results of colorimetric test performed by commercial laboratory.

FIG. 2 shows the mass spectrometric xylose content is very linear with known amounts of xylose added to serum. FIG. 3 compares measurements of xylose content of samples which were obtained from a commercial laboratory performing the colorimetric method of measuring reducing sugars in serum with the results of GC/MS determinations, and shows variations between the linear GC/MS assay and the commercially available colorimetric assay.

Our tests showed CD of twenty-five pre-xylose samples had background absorbance of 0.04±0.02 units, equivalent to a xylose background of 2.7±1.3 mg/dL (range 0.6 to 6.0 mg/dL). However, twenty-one samples of pre-xylose serum examined by GC/MS were found to have a xylose background of 0.21±0.12 mg/dL (range 0–0.5 mg/dL), which is insignificant.

The xylose determinations on 32 sera post xylose administration (content by CD of 3–52 mg/dL) correlated well as a group between the CD and the GC/MS assay (r=0.95), although the results obtained by CD were 10–88% lower than those obtained by GC/MS in 14/32 instances, while CD values were 11%–19% higher in 2/32 instances.

Thus, nonspecific CD of serum xylose has a variable background which is markedly reduced when analysis is carried out by GC/MS; and CD and GC/MS assays for xylose correlate, but potential clinically significant variation exists for any individual sample between GC/MS and CD. Improvement in the clinical accuracy of serum xylose testing is possible through more specific analysis of xylose content in serum by GC/MS.

Figure 4:
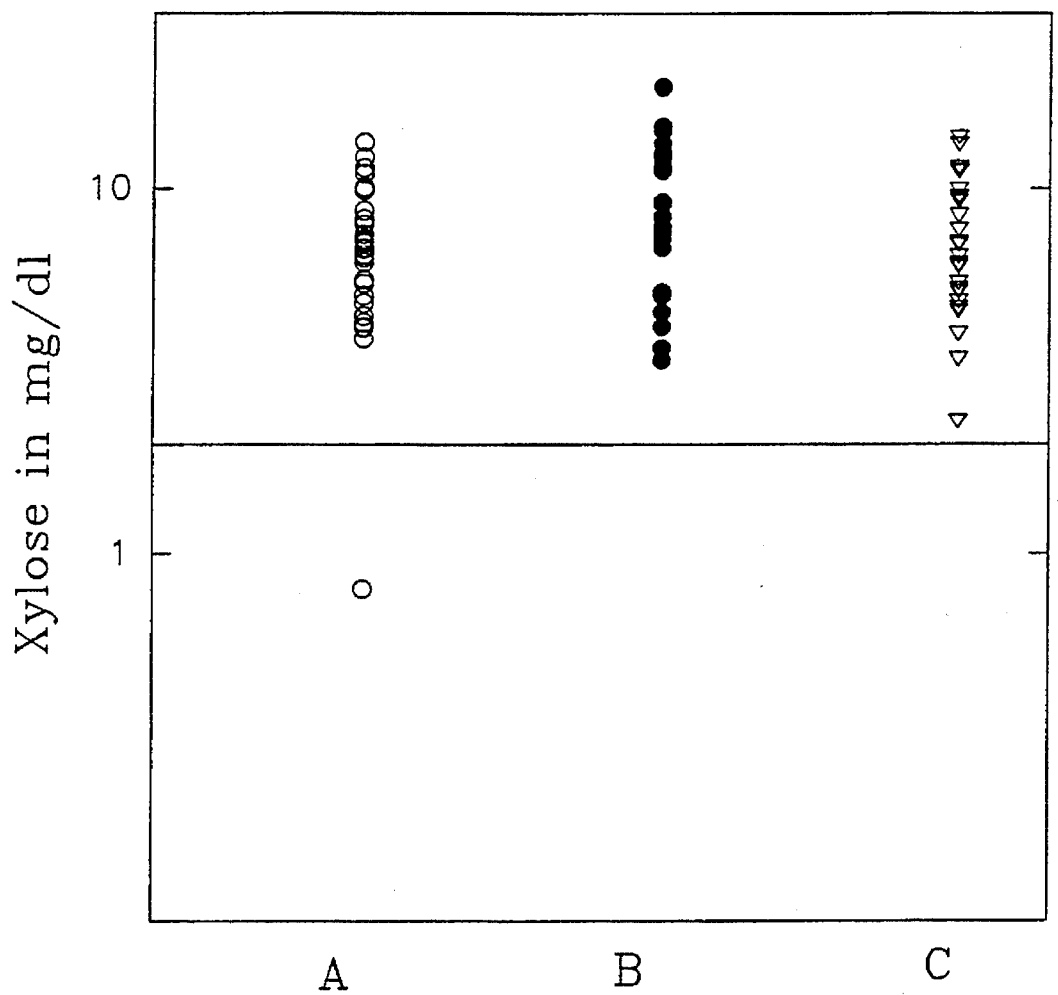
FIG. 4 shows the results of xylose tests of this invention performed concurrently with the bentiromide tests: A=Apparently normal; B=Cystic fibrosis; and C=Suspected pancreatic insufficiency.

FIG. 4 shows the results of xylose analysis when testing in the combined bentiromide-xylose assay. Group A=Apparently normal; Group B=Cystic fibrosis; and Group C=Suspected pancreatic insufficiency. The single low xylose in Group A was an individual who developed viral gastroenteritis within 48 hours of testing.

Example 6

Method of Bentiromide Analysis

Column Preparation

Several types of columns are used in this analysis and these include a strong anion exchange column (SAX), a strong cation exchange column (SCX), and a $C_{18}$ column. The SAX and SCX columns are prepared in disposable plastic columns containing 50 mg of each resin. Prior to use, the column is prepared by a column volume of methanol followed by four washings with four column volumes of water. Eighteen gauge 1 inch needles are placed on the bottom of the columns to facilitate flow. The $C_{18}$ column (100 mg, double frit) is prepared by four washings with methanol in 0.01 molar acetic acid followed by four column volumes of water and followed by a column volume of one normal HCl. In addition, after the final water wash, the first SCX column is prepared by washing with one column volume of 4 molar acetic acid/0.1 normal HCl.

Sample Preparation

Samples consisting of a 0-time and 60-minute time were each prepared by taking 0.5 ml of serum into a 16×100 mm glass test tube. To this 1.45 ml of water was added followed by 50 microliters of 5 molar $NH_4OH$ for a final concentration of 0.125 molar. The sample was then applied to the above SAX column, the column was then washed with four column volumes of 0.05 molar $NH_4OH$, followed by four column volumes of water. The sample was then eluted with 330 microliters of 4 molar acetic acid/0.1 normal HCl×3 for a final volume of 1 ml. The sample in a 12×75 mm glass test tube was then applied to the first SCX column and the effluent was taken into plastic-screw cap 2 ml tubes. Following application of the sample, the column was then washed with 0.45 ml×2 of 4 molar acetic acid/0.1 normal HCl and the wash and effluent were combined in the plastic test tube. These samples were then taken to dryness in a vacuum centrifuge. Following drying, the samples were resuspended in 200 microliters of 6 normal HCl, the caps were placed on tightly and the samples were "cooked" in a 110° C. sand bath for 60 minutes. Following this, the samples were allowed to cool and 1 ml of $H_2O$ was added. The samples were then added to a prepared $C_{18}$ column and the effluent was collected from the 1.2 ml sample and two 1 ml 1 normal HCl washes were added to the sample for a total of 3.2 ml of sample in acid. The sample in 16×100 mm glass test tubes was applied to a second SCX column which had not been pre-equilibrated in 4 molar acetic acid/0.1 normal HCl. After sample application, the column was washed with 4 column volumes of methanol/0.01 molar acetic acid followed by 4 column volumes of water. The sample was then eluted into autosampler vials (ASV) using 350 microliters of 5 molar $NH_4OH \times 3$. The samples in the ASV were then dried down and propionic anhydride (30 microliters) was added for 15–30 minutes at room temperature. The samples in the ASV were again dried and derivatized with tert-butyl derivative (N-methyl-N-t-butyldimethyl-silyltrifluoroacetamide) using 12 microliters of tert-butyl and 18 microliters of acetonitrile. The samples were capped, vortexed three times for 30 seconds on a multiple sample vortexer and placed in an oven at 60° C. for 30 minutes prior to analysis by GC/MS. The analysis was then ready to be carried out on the GC/MS.

Stable Isotopes

Each set of samples had a zero time sample to which 50 ng of $PABA^{M+2}$ (2,6-$[^2H]_2$-PABA) had been added following the first SCX column. The subsequent time samples, i.e. usually 60-minute samples, already contained $PABA^{M+6}$ ($[^{13}C]_6$-PABA) as well as the native PABA from bentiromide. These samples also received 50 ng of $PABA^{M+2}$. With each run of 0 and 60 minute samples on individual patients, three standards prepared in an identical manner using normal human serum were also run. These standards consisted of a high standard (i.e. normal value), a 0.30 standard (i.e. indeterminate range value), and finally, a low standard (i.e. abnormal value). Each of these three standards was run and prepared with each batch of bentiromide samples. These standards assured that the isolation of PABA and stable isotope PABA and analysis by the GC/MS were valid for the samples.

Example 7

Method of Xylose Analysis

Gas chromatography mass spectrometry measurement of xylose in serum taken from patients was carried out according to the following protocol:
Standard=100 micrograms/ml $[^{13}C]_1$-Xylose in $H_2O$, stored at −20° C.

1. Place 25 μl of standard in 12×75 mm borosilicate glass tubes;
2. Add 25 μl of serum to be tested;
3. Vortex for 10 seconds;
4. Add 25 μl of 50% (w/v) trichloroacetic acid;
5. Vortex for 10 seconds;
6. Add 200 μl of deionized water;
7. Vortex for 10 seconds;
8. Centrifuge at 3000 g at 4° C. for 10 minutes;
9. Remove 100 μl supernatant; add the supernatant to 400 μl of $H_2O$ in a separate 12×75 borosilicate glass tube;
10. In a fume hood; add 1.5 ml hydrated ethyl ether, vortex for 30 seconds;
11. Let sample sit for 1 minute then remove the organic (supernatant) phase by aspiration;
12. Add 1.5 ml hydrated ethyl ether, vortex for 30 seconds;
13. Let sample sit for 1 minute then remove the organic (supernatant) phase by aspiration;
14. Dry sample in vacuum centrifuge;
15. Add 12 μl of TBDMS (N-methyl-N-t-butyldimethylsilyltrifluoroacetamide) and 30 μl acetonitrile to dry sample, cover tube with parafilm;
16. Place in 55° C. oven for 2 hours; and
17. Place supernatant fluid into autosampler vial and examine by GC/MS using $^{13}C_1$-xylose as a standard for quantitation The derivatized xylose has four peaks. The ion having an M/Z of 417 eluting at 6.6 minutes was used for measurement.

NOTE: All starting materials used in the following examples are readily available commercially, e.g. from C/D/N Isotopes, Quebec, Canada, Cambridge Isotope Laboratories, Woburn, Mass., or Isotec, Inc., Miamisburg, Ohio.

Example 8

Synthesis of $[^{13}C]_6$-PABA and Other Carbon-labelled PABA Isotopes $[^{13}C]_6$-PABA (4-Aminobenzoic-$[^{13}C]_6$ acid) is obtained from commercially available bromobenzene-$[^{13}C]_6$ by the following reaction sequence: nitration of bromobenzene and separation of isomers as described by Vogel, (*Vogel's Textbook of Practical Organic Chemistry*, 5th ed., Longman, New York, 1989, p. 856); substitution of the bromide with cuprous cyanide using Friedman and Shechter's procedure (L. Friedman and H. Shechter, J. Org. Chem., 1961, 2522); hydrolysis of the nitrile under acidic or basic conditions, and reduction of the nitro group to an amine.

1-Bromo-4-nitrobenzene-$[^{13}C]_6$

Bromobenzene-$[^{13}C]_6$ (5 g) is slowly added to a mixture of concentrated nitric acid (6 mL) and concentrated sulfuric acid (6 mL) over 15 min. The reaction mixture is stirred at room temperature 30 minutes, then heated on a water bath 30 minutes, cooled and poured onto 150 mL of ice-cold water. The precipitate is filtered, washed with water and dried. Purification of the crude product by chromatography on silica gel (elution with hexanes:dichloromethane, 5:1) yields 4.15 g (65%) of 1-bromo-4-nitrobenzene-$[^{13}C]_6$ (m.p. 125° C.) and 1,6 g (25%) of 1-bromo-2-nitrobenzene-$[^{13}C]_6$ (m.p. 40°–41° C.).

4-Nitrobenzo-$[^{13}C]_6$-nitrile

A solution of 1-bromo-4-nitrobenzene-$[^{13}C]_6$ (4.15 g) and of cuprous cyanide (2.5 g) in dimethylformamide (20 mL) is heated to reflux 6 h, cooled slightly and poured onto a solution of ferric chloride hydrate (9.6 g) in 1.7N hydrochloric acid (17 mL). This mixture is heated to 60°–70° C. for 20 minutes, diluted with water (100 mL), filtered, the solids washed with water and dried. The crude product is dissolved in a minimum of dichloromethane and filtered through a short column of silica gel. The yield of 4-nitrobenzo-$[^{13}C]_6$-nitrile (m.p. 145°–146° C.) is 2.5 g (80%).

4-Nitrobenzoic-$[^{13}C]_6$ Acid a) A mixture of 4-nitrobenzo-$[^{13}C]_6$-nitrile (2.5 g), concentrated hydrobromic acid (17 mL) and glacial acetic acid (12.5 mL) is heated to reflux 20 h, cooled in ice, filtered, the solid washed with water and dried 4-Nitrobenzoic-$[^{13}C]_6$ acid (m.p. 137°–139° C.) is produced in 84% yield (2.35 g); or b) 4-Nitrobenzo-[$^{13}$C]$_6$-nitrile (3.0 g) and sodium hydroxide (8 g) in water (100 mL) are heated to reflux 18 h. The cooled reaction mixture is acidified with concentrated hydrochloric acid (20 mL), extracted with ether (5×200 mL), the extracts dried over magnesium sulfate, filtered and evaporated to provide 4-nitrobenzoic-[$^{13}$C]$_6$ acid (2.7 g, 80% yield).

[$^{13}$C]$_6$-PABA (4-Aminobenzoic-[$^{13}$C]$_6$ Acid)

a) Tin powder (6 g) and concentrated hydrochloric acid (13 mL) are cautiously added to 4-nitrobenzoic-[$^{13}$C]$_6$ acid (2.7 g) and the mixture is heated to gentle reflux 30 minutes. After some cooling, the pH is adjusted to 8 with concentrated ammonium hydroxide, the suspension is boiled 20 minutes, filtered hot and washed with hot water. The solution is concentrated to 35 mL and acidified with glacial acetic acid while cooled in ice. The solid is filtered, washed with cold water and dried to provide pure [$^{13}$C]$_6$-PABA (4-aminobenzoic-[$^{13}$C]$_6$ acid) (1.3 g, 58% yield, m.p. 187°–189° C.).

b) A solution of 4-nitrobenzoic-[$^{13}$C]$_6$ acid (2.3 g) in absolute ethanol (150 mL) is hydrogenated at atmospheric pressure over platinum oxide catalyst (0.2 g) until the hydrogen uptake ceases. Filtration of the catalyst, evaporation of the solvent and recrystalization of the residue gives pure [$^{13}$C]$_6$-PABA (4-aminobenzoic-[$^{13}$C]$_6$ acid) (1.4 g, 74% yield).

Example 9

Synthesis of [$^{15}$N]-PABA

Using the procedure of Example 8, and substituting natural bromobenzene for [$^{13}$C]$_6$-bromobenzene and nitric-[$^{15}$N]-acid for natural nitric acid, [$^{15}$N]-PABA (4-amino-[$^{15}$N]-benzoic acid) is produced.

Example 10

Synthesis of α-[$^{13}$C]-PABA

Using the procedure of Example 8, and substituting natural bromobenzene for [$^{13}$C]$_6$-bromobenzene and cuprous [$^{13}$C] cyanide for natural cuprous cyanide, α-[$^{13}$C]-PABA (4-aminobenzoic acid-α-[$^{13}$C]) is produced.

Example 11

Synthesis of α-[$^{13}$C]-[$^{15}$N]-PABA

The procedures of Examples 9 and 10 are combined, substituting natural bromobenzene for [$^{13}$C]$_6$-bromobenzene, nitric [$^{15}$N] acid for natural nitric acid, and cuprous [$^{13}$C] cyanide for natural cuprous cyanide, to obtain α-[$^{13}$C]-[$^{15}$N]-PABA (4-amino-[$^{15}$N]-benzoic acid α-[$^{13}$C].

Example 12

Synthesis of 2,3,5,6-[$^2$H]$_4$-PABA

Using the procedure of Example 8 and substituting [$^2$H]$_5$-bromobenzene for [$^{13}$C]$_6$-bromobenzene, 2,3,5,6-[$^2$H]$_4$-PABA (4-aminobenzoic-2,3,5,6-[$^2$H]$_4$ is produced.

Example 13

2,3,5,6-[$^2$H]$_4$-[$^{15}$N]-PABA

Combining the procedures of Examples 9 and 12, substituting [$^2$H]$_5$-bromobenzene for [$^{13}$C]$_6$ bromobenzene and nitric [$^{15}$N] acid for natural nitric acid, 2,3,5,6-[$^2$H]$_4$-[$^{15}$N]-PABA (4-amino-[$^{15}$N]-benzoic-2,3,5,6-[$^2$H]$_4$ acid) is produced.

Example 14

α-[$^{13}$C]-2,3,5,6-[$^2$H]$_4$-PABA

Combining the procedures of Examples 10 and 12, substituting [$^2$H]$_5$-bromobenzene for [$^{13}$C]$_6$ bromobenzene and cuprous [$^{13}$C] cyanide for natural cuprous cyanide, α-[$^{13}$C]-2,3,5,6-[$^2$H]$_4$-PABA (4-amino-benzoic-2,3,5,6-[$^2$H]$_4$ acid -α-[$^{13}$C]) is produced.

Example 15

α-[$^{13}$C]-2,3,5,6-[$^2$H]$_4$-[$^{15}$N]-PABA

Combining the procedures of Examples 9, 10 and 12, substituting [$^2$H]$_5$-bromobenzene for [$^{13}$C]$_6$ bromobenzene, nitric [$^{15}$N] acid for natural nitric acid and cuprous [$^{13}$C] cyanide for natural cuprous cyanide, α-[$^{13}$C]-2,3,5,6-[$^2$H]$_4$-[$^{15}$N]-PABA (4-amino-[$^{15}$N]-benzoic-2,3,5,6-[$^2$H]$_4$ acid α-[$^{13}$C]) is produced.

Example 16

[$^{13}$C]$_6$-[$^{15}$N]-PABA

Using the procedure of Example 8, substituting nitric [$^{15}$N] acid for natural nitric acid, [$^{13}$C]$_6$-[$^{15}$N]-PABA (4-amino-$^{15}$N-benzoic [$^{13}$C]$_6$ acid) is produced.

Example 17

[$^{13}$C]$_7$-PABA

Using the combined procedures of Examples 8 and 10, substituting cuprous [$^{13}$C]-cyanide for natural cuprous cyanide, [$^{13}$C]$_7$-PABA (4-aminobenzoic acid [$^{13}$C]$_7$) is produced.

Example 18

[$^{13}$C]$_7$-[$^{15}$N]-PABA

Using the combined procedures of Examples 16 and 17, substituting nitric [$^{15}$N] acid for natural nitric acid and cuprous [$^{13}$C] cyanide for natural cuprous chloride, [$^{13}$C]$_7$-[$^{15}$N]-PABA is produced.

As will be readily appreciated by the skilled artisan, any combination of [$^{13}$C]$_6$, [$^{15}$N], [$^2$H] and α-[$^{13}$C] isotopes may be produced by substituting the appropriate starting materials into the basic procedure of Example 8. When 99 atom % $^{13}$C and/or 99 atom % $^{15}$N and/or 98 atom % $^2$H starting materials are used, the enrichment of the 4-aminobenzoic acids obtained is 99 atom % $^3$C and/or 99 atom % $^{15}$N and/or 98 atom % $^2$H.

Example 19

2,6-[$^2$H]$_2$-PABA

Attempts were made to produce 2,6-[$^2$H]$_2$-PABA by back exchanging the 2,3,5,6-[$^2$H]$_4$-PABA product of Example 12, without success, either because of lack of reaction in boiling water, or of extensive decomposition in hot dilute acid. The difficulty was overcome by starting with 4-nitroaniline as its hydrochloric salt and exchanging it in deuterium oxide to provide 4-nitrobenzonitrile-2,6-[$^2$H]$_2$ via a Sandmeyer reaction with alkali cyanides. The latter product is then converted to 2,6-[$^2$H]$_2$-PABA (4-aminobenzoic-2,6-[$^2$H]$_2$ acid) in the same fashion as described in Example 8.

4-Nitroaniline-N,N,2,6-[$^2$H]$_4$ Deuterochloride

A suspension of 4-nitroaniline (21 g) in 1.5N hydrochloric acid (150 mL) is heated until all solids are dissolved. Water is then evaporated and the remaining solid is dried under vacuum. Deuterium oxide (250 g) is added to this solid, the mixture is heated to reflux for two days, the water is removed under vacuum, and the solid is dried. This exchange process is repeated once more with another portion (250 g) of deuterium oxide and provides a quantitative yield (27 g) of 4-nitroaniline-N,N-2,6-[$^2$H]$_4$ deuterochloride ((% $^2$H) D>99%).

4-Nitrobenzonitrile-2,6-[$^2$H]$_2$

A solution of sodium nitrate (8 g) in water (25 mL) is added to a suspension of 4-nitroaniline-N,N-2,6-[$^2$H]$_4$ deuterochloride (18 g) in ice-cold 3N hydrochloric acid (75 mL) while maintaining the temperature below 5° C. The pH is adjusted to 8 with solid sodium carbonate, and this suspension is added over a period of 30 minutes to an ice-cold mixture of freshly prepared cuprous chloride (25 g), sodium cyanide (16.5 g), water (25 mL) and toluene (25 mL), and the reaction mixture is allowed to stir at room temperature overnight. The product is extracted with dichloromethane (3×200 mL), the organic extracts are washed neutral with water, dried over magnesium sulfate and the solvent is evaporated. Recrystallization of the residue in ethanol yields 4-nitrobenzonitrile-2,6-[$^2$H]$_2$ (8.2 g, 54% yield, $^2$H>99%).

The next two steps (i.e. hydrolysis of nitrile and reduction of the nitro group) are performed as in Example 8 to produce 2,6-[$^2$H]$_2$-PABA (4-aminobenzoic-2,5-D$_2$-deuterochloride). When sodium cyanide is replaced with sodium cyanide-[$^{13}$C], α[$^{13}$C]-2,6-[$^2$H]$_2$-PABA (4-amino-benzoic-2,6-[$^2$H]$_2$ acid-α-[$^{13}$C]) is obtained.

Example 20

Alternative Synthesis of [$^{13}$C]$_6$-2,6-[$^2$H]$_2$-PABA

[$^{13}$C]$_6$-2,6-[$^2$H]$_2$-PABA and additional labelled isotopes may be prepared from commercially available aniline-[$^{13}$C]$_6$ by acetylation of the amine, followed by nitration of the ring and hydrolysis of the amide in deuterochloric acid to produce 4-nitroaniline-[$^{13}$C]$_6$-N,N-2,6-[$^2$H]$_4$-deuterochloride. The latter product is then converted into [$^{13}$C]$_6$-2,6-[$^2$H]$_2$-PABA (4-aminobenzoic-[$^{13}$C]$_6$-2,6-[$^2$H]$_2$ acid.

Acetanilide-[$^{13}$C]$_6$

To a solution of aniline-[$^{13}$C]$_6$ (5 g) in 0.44N hydrochloric acid (125 mL) is added acetic anhydride (6.8 g), followed by a solution of sodium acetate (8 g) in water (25 mL). The mixture is stirred vigorously 30 min, cooled in ice, filtered, the solid is washed with water and dried. The yield of acetanilide-[$^{13}$C]$_6$ (m.p. 113° C.) is 5.9 g (83%).

4-nitroacetanilide-[$^{13}$C]$_6$

Concentrated sulfuric acid (12 mL) is added slowly to a suspension of acetanilide-[$^{13}$C]$_6$ (5.9 g) in acetic acid (10 mL); the resulting solution is cooled in ice and a mixture of concentrated nitric acid (2.6 mL) and concentrated sulfuric acid (1.7 mL) is added dropwise while keeping the temperature below 10° C. The reaction mixture is allowed to warm to room temperature over one hour, then is poured onto ice-cold water (150 mL) and stirred 15 min. The solid is filtered, washed with cold water, dried and recrystallized in ethanol to provide pure 4-nitroacetanilide-[$^{13}$C]$_6$ (4.7 g, 60% yield, m.p. 214° C.).

4-nitroacetanilide-[$^{13}$C]$_6$-N,N,2,6-[$^2$H]$_4$-deuterochloride

A mixture of 4-nitroacetanilide-[$^{13}$C]$_6$ (4.7 g), concentrated deuterochloric acid (75 g) and deuterium oxide (75 g) is heated to reflux for 24 hours, cooled and evaporated to dryness. Deutrium oxide (100 g) is added to the resulting solid, the mixture is heated to reflux for two days, the water is evaporated and the solid is dried to provide pure 4-[$^{13}$C]$_6$-N,N2,6-[$^2$H]$_4$ deuterochloride (4.5 g, 96% yield).

[$^{13}$C]$_6$-2,6-[$^2$H]$_2$-PABA

The 4-nitroaniline-[$^{13}$C]$_6$-N,N-2,6-[$^2$H]$_4$-deuterochloride is converted into [$^{13}$C]$_6$-2,6-[$^2$H]$_2$-PABA (4-aminobenzoic-[$^{13}$C]$_6$-2,6-[$^2$H]$_2$ acid) as described above in Example 19.

Example 21

[$^{15}$N]-2,6-[$^2$H]$_{2\text{-}PABA}$

[$^{15}$N]-N-2,6-[$^2$H]-PABA (4-aminobenzoic-[$^{15}$N]-2,6-[$^2$H]$_2$ acid) may be prepared by the procedure of Example 20, substituting natural aniline for [$^{13}$C]$_6$-aniline and nitric-[$^{15}$N] acid for natural nitric acid.

Example 22

α-[$^{13}$C]-[$^{15}$N]-2,6-[$^2$H]$_2$-PABA

α[$^{13}$C]-[$^{15}$N]-2,6-[$^2$H]$_2$-PABA (4-aminobenzoic-[$^{15}$N]-2,6-[$^2$H]$_2$ acid-α-[$^{13}$C]) may be prepared by the procedure of Example 21, substituting sodium cyanide-[$^{13}$C] for sodium cyanide.

Example 23

[$^{13}$C]$_6$-[$^{15}$N]-2,6-[$^2$H]$_2$-PABA

[$^{13}$C]$_6$-[$^{15}$N]-2,6-[$^2$H]$_2$-PABA (4-aminobenzoic-[$^{15}$N]-[$^{13}$C]$_6$-2,6-[$^2$H]$_2$ acid) may be prepared by the procedure of Example 20, substituting nitric-[$^{15}$N] acid for natural nitric acid.

Example 24

α-[$^{13}$C]-[$^{13}$C]$_6$-2,6-[$^2$H]$_2$-PABA

α-[$^{13}$C]-[$^{13}$C]$_6$-2,6-[$^2$H]$_2$)-PABA (4-aminobenzoic-[$^{13}$C]$_6$-2,6-[$^2$H]$_2$ acid-α-[$^{13}$C]) may be prepared by the procedure of Example 20 substituting sodium cyanide-[$^{13}$C] for sodium cyanide.

Example 25

α-[$^{13}$C]-[$^{13}$C]$_6$-[$^{15}$N]-2,6-[$^2$H]$_2$-PABA (4-aminobenzoic-[$^{15}$N]-[$^{13}$C]$_6$-2,6-[$^2$H]$_2$ acid-α-[$^{13}$C]) may be prepared by the procedure of Example 24, substituting nitric-[$^{15}$N] acid for natural nitric acid.

As will be readily appreciated by those skilled in the art, combinations and permutations of the above procedures may be performed to yield additional isotopes such that PABA isotopes having molecular weights from 138–154 may be produced. These isotopes can then be converted to the corresponding bentiromide isotopes as described above.

While the invention has been particularly shown and described with reference to preferred embodiments thereof, it will be understood by those skilled in the art that the foregoing and other modifications or changes in form and detail may be made therein without departing from the spirit and scope of the invention.

We claim:

1. A method of using a non-radioactive isotope of PABA capable of being absorbed through a patient's digestive tract and passing into urine or serum for evaluating pancreatic and small bowel function in a patient comprising:
    a) obtaining a first 0-time fluid sample from the patient and measuring natural PABA concentration therein;
    b) administering to said patient a known quantity of bentiromide along with a known quantity of xylose;
    c) administering with said bentiromide and xylose a non-radioactive isotope of PABA selected from the group consisting of [$^{13}$C]$_6$-PABA and 2,6-[$^2$H]$_2$-PABA, having a molecular weight different from natural PABA;
    d) allowing sufficient time for said xylose, bentiromide and PABA isotope to be absorbed through the patient's digestive tract and pass into said fluid;
    e) obtaining a second later time sample of said fluid from said patient, and measuring the xylose, natural PABA and isotope PABA therein using gas chromatography mass spectroscopy wherein said PABA measurement specifically measures PABA rather than other arylamines; and
    f) comparing said measured amount of natural PABA in said 0-time sample, said administered amounts of xylose, isotope PABA, and bentiromide, and said measured amounts of xylose, natural PABA and isotope PABA in said later-time sample to determine the proportion of administered bentiromide converted to natural PABA in the patient's body, said proportion being indicative of pancreatic function, and said measured amount of xylose is compared with said administered amount of xylose to determine the proportion of xylose absorbed in the digestive tract of said patient, said proportion being indicative of small bowel disease.

2. A method of using a non-radioactive isotope of PABA capable of being absorbed through a patient's digestive tract and passing into urine or serum for screening pancreatic function in a patient comprising:
    a) obtaining a first 0-time fluid sample from the patient and measuring natural PABA concentration therein;
    b) administering to said patient a known quantity of bentiromide;
    c) administering with said bentiromide a non-radioactive isotope of PABA selected from the group consisting of [$^{13}$C]$_6$-PABA and 2,6-[$^2$H]$_2$-PABA, having a molecular weight different from natural PABA;
    d) allowing sufficient time for said bentiromide and PABA isotope to be absorbed through the patient's digestive tract and pass into said fluid;
    e) obtaining a second later time sample of said fluid from said patient, and measuring the natural PABA and isotope PABA therein by mass spectroscopy wherein said PABA measurement specifically measures PABA rather than other arylamines; and
    f) comparing said measured amount of natural PABA in said 0-time sample, said administered amounts of bentiromide and isotope PABA, and said measured amounts of natural PABA and isotope PABA to determine the proportion of administered bentiromide converted to natural PABA in the patient's body, said proportion being indicative of pancreatic function.

3. The method of claim 2 wherein said fluid samples are serum samples.

4. The method of claim 2 wherein said administered amounts of bentiromide are between about 6 mg and about 7 mg and said administered amounts of isotope PABA are between about 2.0 mg and about 2.5 mg.

5. The method of claim 2 wherein a second isotope of PABA having a molecular weight different from natural PABA and from said administered isotope of PABA is added to said second fluid sample prior to said measurements to provide a standard for said measurements.

6. The method of claim 2 wherein xylose is administered to said patient with said bentiromide and measured in said second fluid sample, and said measured amount of xylose is compared with said administered amount of xylose to determine the proportion of said xylose absorbed in the digestive tract of said patient, said proportion being indicative of small bowel function in said patient.

7. A method of using a non-radioactive isotope of PABA for evaluating pancreatic function in a patient comprising:
    a) administering to said patient a known quantity of a non-radioactive isotope of bentiromide selected from the group consisting of N-benzoyl-tyrosyl 2,6-[$^2$H]$_2$-PABA and N-benzoyl-tyrosyl $^{13}$[C]$_6$-PABA having a molecular weight different from natural bentiromide;
    b) administering with said isotope of bentiromide a non-radioactive isotope of PABA having a mass different from the PABA portion of said isotope of bentiromide;
    c) allowing sufficient time for said isotope of bentiromide to be absorbed through the patient's digestive tract;
    d) obtaining a fluid sample from said patient, and measuring the isotopes of PABA therein; and
    e) comparing said administered amounts of bentiromide and PABA isotopes and said measured amounts of PABA isotopes in said fluid sample, to determine the proportion of administered isotope bentiromide converted to isotope PABA in the patient's body, said proportion being indicative of pancreatic function.

8. The method of claim 7 wherein said fluid sample is a serum sample.

9. The method of claim 7 wherein said measurements are performed by mass spectroscopy.

10. The method of claim 7 wherein said administered amount of isotope bentiromide is between about 6 mg and about 7 mg.

11. The method of claim 7 wherein xylose is administered to said patient with said isotope bentiromide and measured in said fluid sample, and said measured amount of xylose is compared with said administered amount of xylose to determine the proportion of said xylose absorbed in the digestive tract of said patient, said proportion being indicative of small bowel function in said patient.

* * * * *

UNITED STATES PATENT AND TRADEMARK OFFICE
CERTIFICATE OF CORRECTION

PATENT NO. : 5,506,147

DATED : April 9, 1996

INVENTOR(S) : Kolhouse et al.

It is certified that error appears in the above-identified patent and that said Letters Patent is hereby corrected as shown below:

Column 24, lines 42 and 43:

In claim 7, subparagraph c), please insert --to be processed in and the PABA isotopes-- between "bentiromide" and "to be".

Signed and Sealed this

Thirteenth Day of August, 1996

Attest:

BRUCE LEHMAN

Attesting Officer     Commissioner of Patents and Trademarks